(12) United States Patent
Chu et al.

(10) Patent No.: US 11,607,533 B2
(45) Date of Patent: Mar. 21, 2023

(54) TATTOO NEEDLE STRUCTURE

(71) Applicant: NATIONAL TAIWAN UNIVERSITY OF SCIENCE AND TECHNOLOGY, Taipei (TW)

(72) Inventors: Jinn Chu, Taipei (TW); Wen-Che Liao, Taipei (TW); Pak-Man Yiu, Taipei (TW)

(73) Assignee: NATIONAL TAIWAN UNIVERSITY OF SCIENCE AND TECHNOLOGY, Taipei (TW)

( * ) Notice: Subject to any disclaimer, the term of this patent is extended or adjusted under 35 U.S.C. 154(b) by 471 days.

(21) Appl. No.: 16/868,532

(22) Filed: May 6, 2020

(65) Prior Publication Data

US 2021/0260352 A1 Aug. 26, 2021

(30) Foreign Application Priority Data

Feb. 20, 2020 (TW) .................................. 109105507

(51) Int. Cl.
*A61M 37/00* (2006.01)
*A61L 31/02* (2006.01)
*A61L 31/08* (2006.01)
*C23C 14/16* (2006.01)
*C23C 14/35* (2006.01)

(52) U.S. Cl.
CPC ....... *A61M 37/0084* (2013.01); *A61L 31/022* (2013.01); *A61L 31/088* (2013.01); *C23C 14/165* (2013.01); *C23C 14/35* (2013.01); *A61L 2420/02* (2013.01)

(58) Field of Classification Search
CPC .............. A61M 37/00; A61M 37/0076; A61M 37/0084; A61M 2037/0053; A61M 2037/0061; A61M 5/3297; A61M 25/0084; A61M 2025/0085; A61M 2025/0087; A61M 2025/0089; A61M 2025/0095; A61M 2205/0238; A61D 7/00; A61L 31/022; A61L 31/088; A61L 2420/02; C23C 14/165; C23C 14/35
See application file for complete search history.

(56) References Cited

U.S. PATENT DOCUMENTS

| 2004/0116953 A1* | 6/2004 | Dixon ............... A61M 37/0076 606/186 |
| 2016/0256636 A1* | 9/2016 | Scherkowski ........ A61M 37/00 |
| 2019/0201674 A1* | 7/2019 | Stoeber ............. A61M 37/0015 |

\* cited by examiner

*Primary Examiner* — Robert A Lynch
(74) *Attorney, Agent, or Firm* — Chih Feng Yeh; Huntington IP Consulting Co., Ltd.

(57) ABSTRACT

A tattoo needle structure is provided. A tattoo needle has a plurality of needle tips, an ink holding space is formed by the arrangement of the needle tips, and a multi-component alloy film is deposited on each needle tip of the tattoo needle by sputtering technology, so that when the tattoo needle is dipped into the tattoo ink, the tattoo ink does not stick to the surface of the multi-component alloy film by the hydrophobic property of the multi-component alloy film, and the tattoo ink is contained in the ink holding space by the cohesive property of the tattoo ink. Thus, when the tattoo needle is dipped into the tattoo ink and the tattoo process is performed, the dyeing area of the skin with the tattoo ink is the cross-sectional area of the ink holding space, thereby achieving the technical effect of improving the contouring resolution of a tattoo.

8 Claims, 10 Drawing Sheets

|  | Block tattoo ink | Red tattoo ink | Blue tattoo ink | Green tattoo ink |
|---|---|---|---|---|
| without the sputter-deposited multi-component alloy film 1 | 12.25 | 30.17 | 43.78 | 24.00 |
| without the sputter-deposited multi-component alloy film 2 | 11.34 | 30.06 | 42.49 | 26.46 |
| without the sputter-deposited multi-component alloy film 3 | 13.63 | 30.96 | 45.16 | 24.13 |
| without the sputter-deposited multi-component alloy film 4 | 15.35 | 30.37 | 45.34 | 25.39 |
| without the sputter-deposited multi-component alloy film 5 | 15.33 | 29.22 | 43.67 | 26.36 |
| with the sputter-deposited Zr-based multi-component alloy film 1 | 42.59 | 49.86 | 65.65 | 31.96 |
| with the sputter-deposited Zr-based multi-component alloy film 2 | 43.94 | 53.94 | 60.15 | 32.15 |
| with the sputter-deposited Zr-based multi-component alloy film 3 | 45.71 | 57.83 | 64.08 | 33.72 |
| with the sputter-deposited Zr-based multi-component alloy film 4 | 43.37 | 49.59 | 68.22 | 32.54 |
| with the sputter-deposited Zr-based multi-component alloy film 5 | 44.11 | 53.21 | 62.24 | 33.43 |

FIG. 3A

|  | Block tattoo ink | Red tattoo ink | Blue tattoo ink | Green tattoo ink |
|---|---|---|---|---|
| with the sputter-deposited W-based multi-component alloy film 1 | 33.70 | 44.61 | 59.43 | 31.27 |
| with the sputter-deposited W-based multi-component alloy film 2 | 28.83 | 43.45 | 57.15 | 30.60 |
| with the sputter-deposited W-based multi-component alloy film 3 | 30.84 | 44.01 | 58.51 | 31.68 |
| with the sputter-deposited W-based multi-component alloy film 4 | 31.68 | 44.13 | 57.01 | 31.10 |
| with the sputter-deposited W-based multi-component alloy film 5 | 31.10 | 46.32 | 58.38 | 30.04 |
| with the sputter-deposited Al-based multi-component alloy film 1 | 28.54 | 32.51 | 52.25 | 27.15 |
| with the sputter-deposited Al-based multi-component alloy film 2 | 25.61 | 33.96 | 50.18 | 27.02 |
| with the sputter-deposited Al-based multi-component alloy film 3 | 26.15 | 33.56 | 55.93 | 26.16 |
| with the sputter-deposited Al-based multi-component alloy film 4 | 27.53 | 33.83 | 52.71 | 26.19 |
| with the sputter-deposited Al-based multi-component alloy film 5 | 25.28 | 32.64 | 51.97 | 26.49 |

FIG. 3B

| average water contact angle data |||||
|---|---|---|---|---|
| | Block tattoo ink | Red tattoo ink | Blue tattoo ink | Green tattoo ink |
| without the sputter-deposited multi-component alloy film | 13.58 | 30.16 | 44.09 | 25.27 |
| with the sputter-deposited Zr-based multi-component alloy film ($Zr_{60}Cu_{25}Al_{10}Cu_5$) | 43.94 | 52.89 | 64.07 | 32.76 |
| with the sputter-deposited W-based multi-component alloy film ($W_{40}Ni_{35}B_{25}$) | 31.23 | 44.50 | 58.10 | 30.94 |
| with the sputter-deposited Al-based multi-component alloy film ($Al_{95}Ni_2Y_3$) | 26.62 | 33.30 | 52.61 | 26.60 |

| Composition | The multi-component alloy film has the following composition in atomic percentage | | |
|---|---|---|---|
| | DC 1 kW | HIPIMS 1 kW | HIPIMS 2.5 kW |
| Zr | 56.61 ± 0.37 | 60.69 ± 0.19 | 59.36 ± 0.33 |
| Cu | 24.79 ± 0.23 | 22.94 ± 0.17 | 24.21 ± 0.21 |
| Al | 12.33 ± 0.08 | 10.44 ± 0.26 | 10.24 ± 0.1 |
| Ni | 6.27 ± 0.11 | 5.93 ± 0.2 | 6.19 ± 0.12 |

FIG. 10

TATTOO NEEDLE STRUCTURE

CROSS-REFERENCE STATEMENT

The present application is based on, and claims priority from TAIWAN patent application serial number 109105507 which was filed on Feb. 20, 2020, the disclosure of which is hereby incorporated by reference in its' entirety.

BACKGROUND

1. Technical Field

The present invention relates to a tattoo needle structure. In particular, the invention pertains to a tattoo needle structure including a tattoo needle with multiple needle tips, wherein a multi-component alloy film is deposited on each needle tip by sputtering technology, and tattoo ink is concentrated in an ink holding space during tattooing through the hydrophobicity of the multi-component alloy film, thereby improving the contouring resolution of a tattoo.

2. Related Art

In tattoo technology, needle tools can be divided into two categories due to different functions, one is the needle tool used for outlining a tattoo, and the other is the needle tool created for coloring a tattoo. With the increasing complexity of tattoo images, the accuracy required is increasing, and the characteristics of current needle tools must be improved in order to achieve the effect of improving the delicateness of the tattoo images and the comfort level for puncturing the skin at the same time, which is the goal of current research and development.

There is still a problem of insufficient accuracy for the existing tattoo needle tools used for outlining a tattoo. When the tattoo image is viewed at a distance, the overall outlines of the tattoo image can be seen, and the viewer does not think that there is any abnormality in the outlines of the tattoo image. But when the tattoo pattern is viewed at close range, it can be clearly seen that the outlines of the tattoo image are blurred.

In summary, it can be seen that there is a problem of insufficient accuracy for the existing tattoo needle tools used for outlining a tattoo. Therefore, it is necessary to propose an improved technical solution to solve this problem.

SUMMARY

In view of the prior art, there is a problem of insufficient accuracy for the existing tattoo needle tools used for outlining a tattoo, the present invention discloses a tattoo needle structure.

The tattoo needle structure disclosed in the present invention includes a tattoo needle and a multi-component alloy film.

The tattoo needle has a plurality of needle tips, and an ink holding space is formed through the arrangement of the plurality of needle tips. The multi-component alloy film is deposited on the plurality of needle tips by sputtering technology.

When the tattoo needle is dipped into tattoo ink, the tattoo ink does not stick to the surface of the multi-component alloy film by the hydrophobic property of the multi-component alloy film, and the tattoo ink is concentrated and contained in the ink holding space by the arrangement of the plurality of needle tips and the cohesive property of the tattoo ink, so that the dyeing area of the skin with the tattoo ink is the cross-sectional area of the ink holding space when the tattoo needle is dipped into the tattoo ink and a tattooing procedure is performed.

The tattoo needle structure disclosed in the present invention is as above. The difference from the prior art is that the tattoo needle has the plurality of needle tips, the arrangement of the needle tips forms the ink holding space, and the multi-component alloy film is disposed on each needle tip by sputtering technology; when the tattoo needle is dipped into the tattoo ink, the tattoo ink dose not stick to the surface of the multi-component alloy film by the hydrophobic property of the multi-component alloy film, and the tattoo ink is concentrated and contained in the ink holding space by the cohesive property of the tattoo ink, so that when the tattoo needle is dipped into tattoo ink and the tattooing process is performed, the dyeing area of the skin with the tattoo ink is the cross-sectional area of the ink holding space.

By the above-mentioned technical solution, the present invention can achieve the technical effect of improving the contouring resolution of a tattoo.

BRIEF DESCRIPTION OF THE DRAWINGS

The structure, operating principle and effects of the present invention will be described in detail by way of various embodiments which are illustrated in the accompanying drawings.

DETAILED DESCRIPTION

The following embodiments of the present invention are herein described in detail with reference to the accompanying drawings. These drawings show specific examples of the embodiments of the present invention. These embodiments are provided so that this disclosure will be thorough and complete, and will fully convey the scope of the invention to those skilled in the art. It is to be acknowledged that these embodiments are exemplary implementations and are not to be construed as limiting the scope of the present invention in any way. Further modifications to the disclosed embodiments, as well as other embodiments, are also included within the scope of the appended claims. These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts.

It is to be acknowledged that, although the terms 'first', 'second', 'third', and so on, may be used herein to describe various elements, these elements should not be limited by these terms. These terms are used only for the purpose of distinguishing one component from another component. Thus, a first element discussed herein could be termed a second element without altering the description of the present disclosure. As used herein, the term "or" includes any and all combinations of one or more of the associated listed items.

It will be acknowledged that when an element or layer is referred to as being "on," "connected to" or "coupled to" another element or layer, it can be directly on, connected or coupled to the other element or layer, or intervening elements or layers may be present. In contrast, when an element is referred to as being "directly on," "directly connected to" or "directly coupled to" another element or layer, there are no intervening elements or layers present.

In addition, unless explicitly described to the contrary, the word "comprise", "include" and "have", and variations such as "comprises", "comprising", "includes", "including", "has" and "having" will be acknowledged to imply the inclusion of stated elements but not the exclusion of any other elements.

Figure 1:
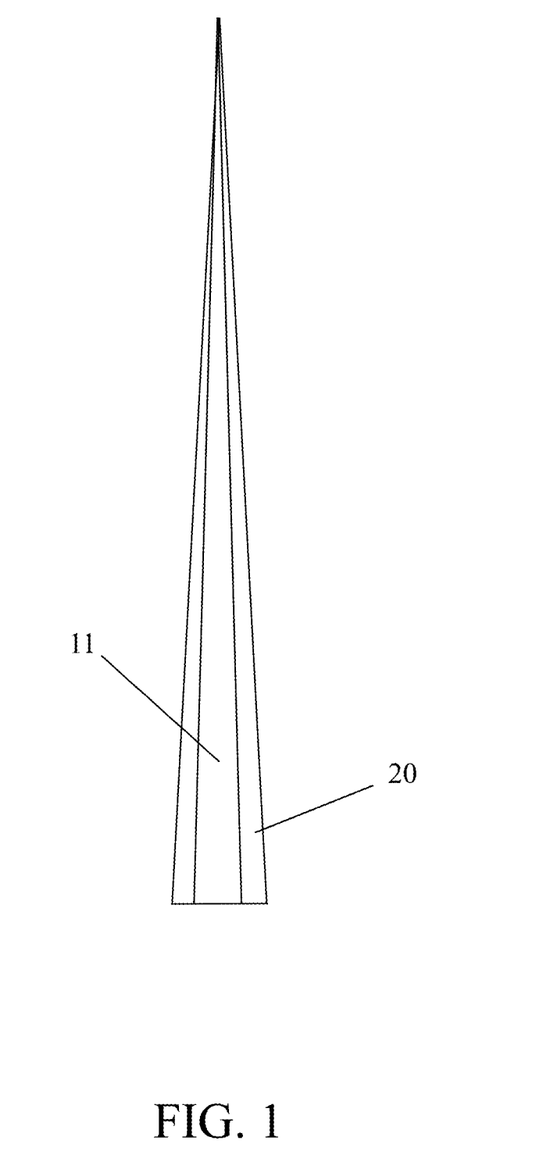
FIG. 1 shows a plan view of a needle tip of a tattoo needle structure of the present invention.

The following first describes a tattoo needle structure disclosed in the present invention, and please refer to FIG. 1, which is a plan view of a needle tip of a tattoo needle structure of the present invention.

The tattoo needle has a plurality of needle tips 11. In FIG. 1, only a single needle tip 11 is used as an illustration of each needle tip. In the present invention, a multi-component alloy film 20 is deposited on the surface of the needle tip 11 of the tattoo needle by sputtering technology. The needle tip 11 shown in FIG. 1 is presented in a more exaggerated manner, and the present invention is not limited thereto.

The above-mentioned multi-component alloy film 20 may be a Zr-based multi-component alloy film including an element combination of Zr, Cu, Al, and Ni; an element combination of Zr, Al, and Co; an element combination of Zr, Cu, Al, and Ta; an element combination of Zr, Cu, Al, and Ag; an element combination of Zr, Cu, Al, Ni, and Ti; an element combination of Zr, Al, Cu, Ti, and Be; an element combination of Zr, Cu, Al, Ni, and Si; an element combination of Zr, Cu, Al, Ni, and Nb; an element combination of Zr, Hf, Ti, Cu, Ni and Al; or an element combination of Zr, Ti, Cu, Ni, Be, Y, and Mg. The multi-component alloy film 20 may be a Ti-based multi-component alloy film including an element combination of Ti, Zr, Cu, Nb, and Co; an element combination of Ti, Zr, Cu, and Ni; an element combination of Ti, Ni, Cu, Sn, and Be; an element combination of Ti, Zr, Hf, Ni, and Cu; an element combination of Ti, Cu, Ni, Si, and B; an element combination of Ti, Zr, Ni, Cu, and Be; or an element combination of Ti, Cu, Ni, Zr, Al, Si, and B. The above-mentioned multi-component alloy film 20 may be a Pd-based multi-component alloy film including an element combination of Pd, Cu, and Si; an element combination of Pd, Ni, and P; or an element combination of Pd, Ni, Cu, and P. The above-mentioned multi-component alloy film 20 may be Fe-base multi-component alloy film including an element combination of Fe, Co, Sm, and B; an element combination of Fe, Co, Tb, and B; an element combination of Fe, Co, Nd, Dy, and B; an element combination of Fe, Co, Ni, Zr, and B; an element combination of Fe, Co, Ni, Si and B; an element combination of Fe, Zr, Co, Mo, W, and B; or an element combination of Fe, Cr, Mo, Er, C, and B. The above multi-component alloy film 20 may be a Cu-based multi-component alloy film including an element combination of Cu, Hf, and Ti; Cu, Zr, and Al; an element combination of Cu, Zr And Nb; an element combination of Cu, Zr, Al, and Ag; an element combination of Cu, Zr, Ti, and Ni; an element combination of Cu, Zr, Al, and Y; an element combination of Cu, Zr, Al, and Ti; or an element combination of Cu, Zr, Hf, and Ti. The multi-component alloy film 20 may be Ni-based multi-component alloy films including an element combination of Ni, Zr, and Al; an element combination of Ni, Nb, and Ta; an element combination of Ni, Nb, and Sn; an element combination of Ni, Nb, Hf, and Ti; an element combination of Ni, Zr, Al, and Nb; an element combination of Ni, Zr, Ti, and Al; an element combination of Ni, Zr, Ti, and Pd; an element combination of Ni, Nb, Ti, and Zr; an element combination of Ni, Cu, Zr, Ti, and Al; an element combination of Ni, Cu, Zr, Ti, Al, and Si; or an element combination of Ni, Nb, Cr, Mo, P, and B. The above multi-component alloy film 20 may be an Al-based multi-component alloy film including an element combination of Al, Ni, and Mn; an element combination of Al, Ni, and Y; an element combination of Al, V, and M; an element combination of Al, Ni, and Ce; an element combination of Al, Co, and Y; an element combination of Al, Ni, Y, Zr, and Co; or an element combination of Al, Ni, Y, Co, and Cu. The multi-component alloy film 20 may be a W-based multi-component alloy film including an element combination of W, Ni, and B; or an element combination of W, Zr, and Si. The multi-component alloy film 20 can a Mg-based multi-component alloy film including an element combination of Mg, Cu, and Y; an element combination of Mg, Ni, and Nd; an element combination of Mg, Cu, and Gd; an element combination of Mg, Al, Cu, and Y; an element combination of Mg, Cu, Y, and Si; an element combination of Mg, Cu, Zn, and Y; or an element combination of Mg, Cu, Ni, Zn, Ag, and Y. The above are all examples, which do not limit the application scope of the present invention.

Figure 2A:
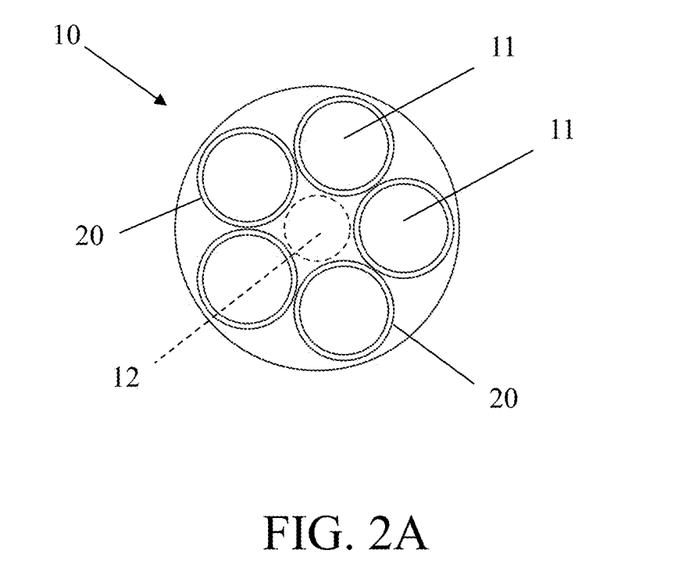
FIG. 2A and FIG. 2B are plan views of the tattoo needle of the tattoo needle structure of the present invention.
Figure 2B:
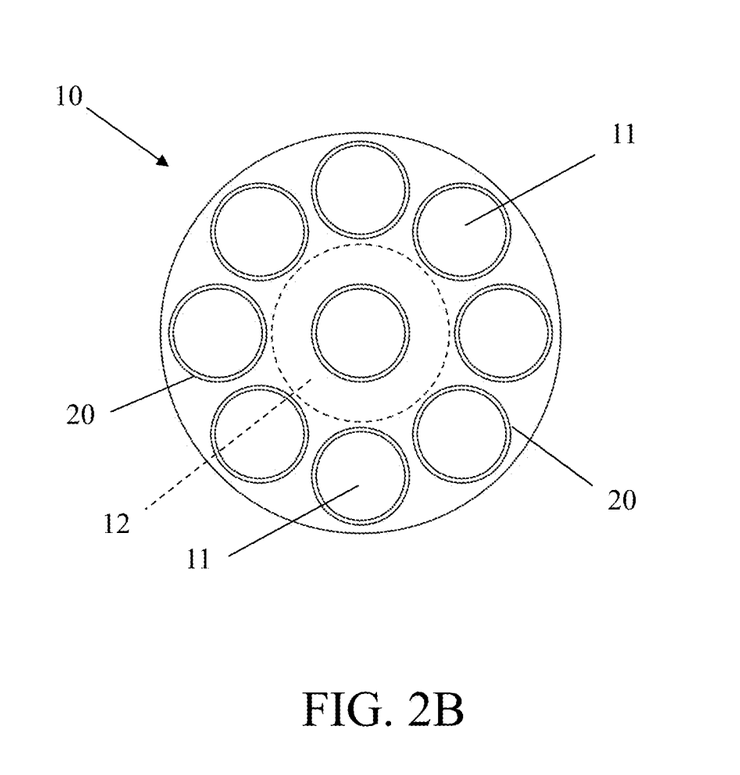

Please refer to FIG. 2A and FIG. 2B, wherein FIG. 2A and FIG. 2B are plan views of the tattoo needle of the tattoo needle structure of the present invention.

The tattoo needle structure disclosed in the present invention includes: a tattoo needle 10 and a multi-component alloy film 20 (refer to FIG. 1). The tattoo needle 10 has a plurality of needle tips 11, the arrangement of the needle tips 11 forms an ink holding space 12, and the multi-component alloy film 20 is deposited on each needle tip 11 of the tattoo needle 10 by sputtering technology. It is worth noting that the thickness of the multi-component alloy film 20 is between 50 nm and 200 nm. This is for illustration only, and does not limit the application scope of the present invention. The multi-component alloy film 20 has an amorphous structure and lacks a long-range and ordered atomic periodicity, which can reduce the damage caused by lattice or grain boundary defects and make its mechanical strength higher. The multi-component alloy film 20 also has the characteristics of high strength, low coefficient of friction, wear resistance, good biocompatibility with not easily sticking to cells, etc.

In FIG. 2A, the tattoo needle 10 has five needle tips 11 which are arranged in a circle, and the inside of the circular arrangement of the five needle tips 11 is the ink holding space 12. In FIG. 2B, the tattoo needle 10 has eight needle tips 11 which are arranged in a circle, the inside of the circular arrangement of the eight needle tips 11 is the ink holding space 12, and an additional needle tip 13 may be provided in the ink holding space 12. Such arrangements of the needle tips 11 included in the tattoo needle 10 are for illustrative purposes only and not used to limit the scope of application of the present invention.

Figure 3A:
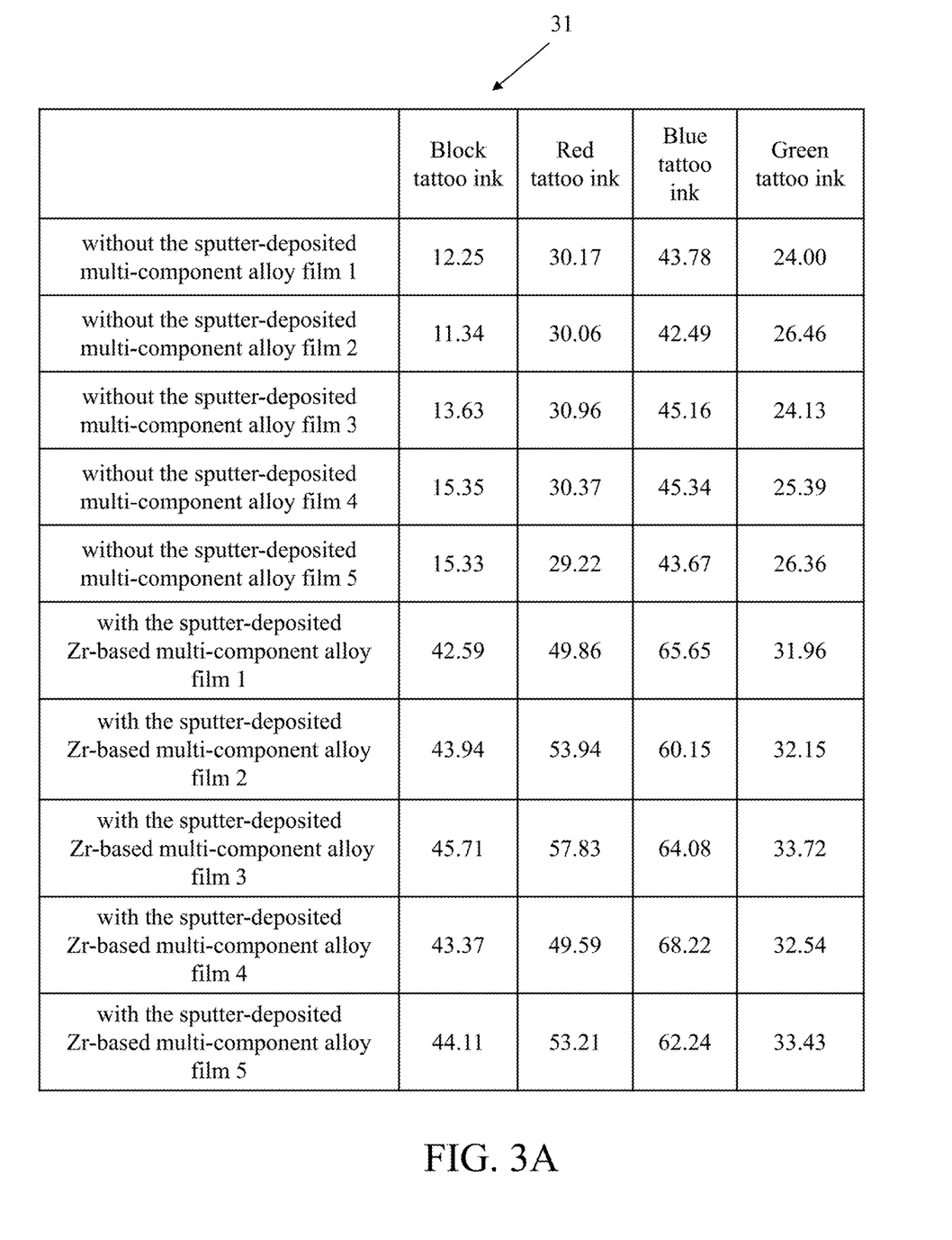
FIG. 3A and FIG. 3B show water contact angles of different tattoo inks of different tattoo needle structures of the present invention.
Figure 3B:
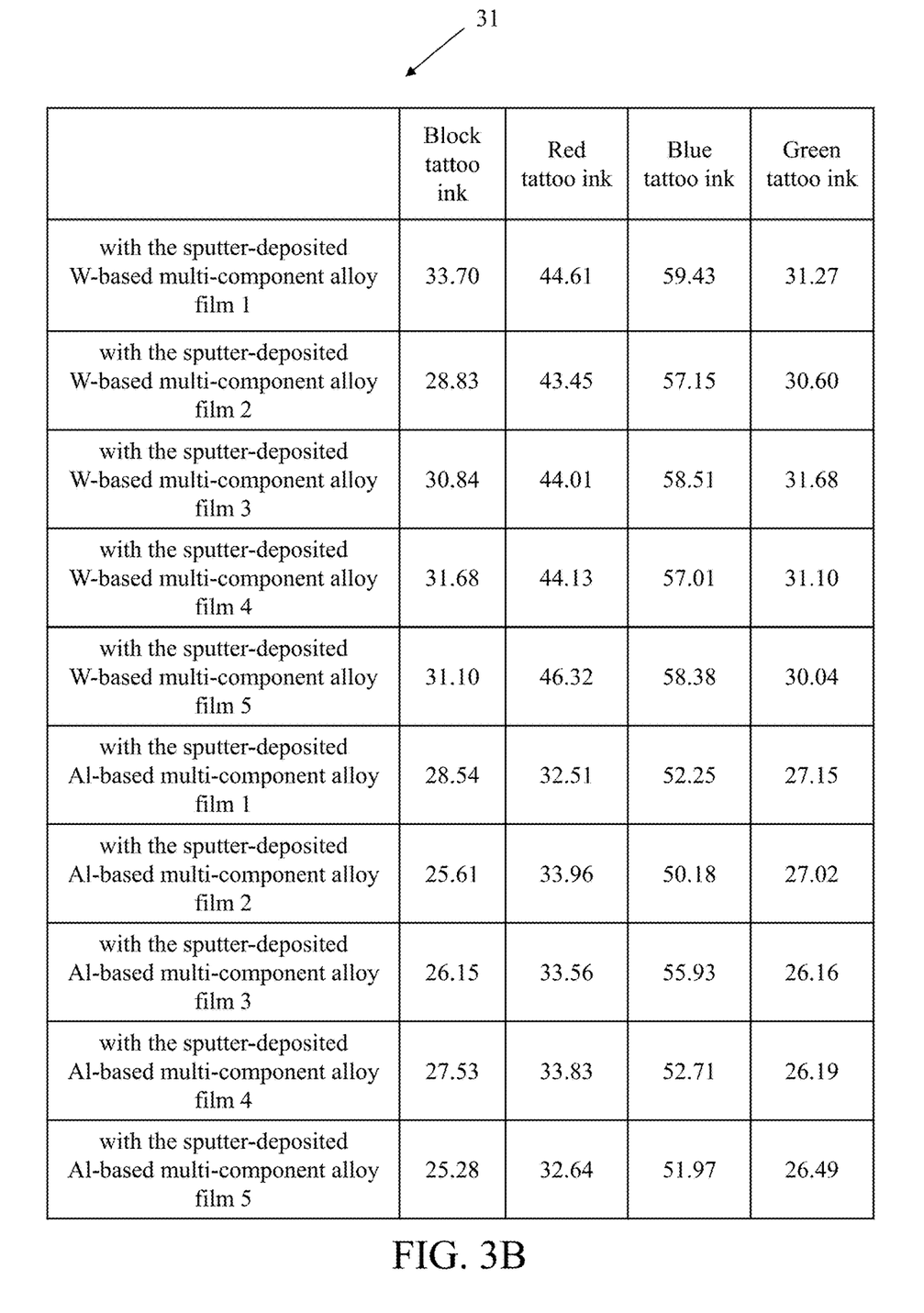
Figure 3C:
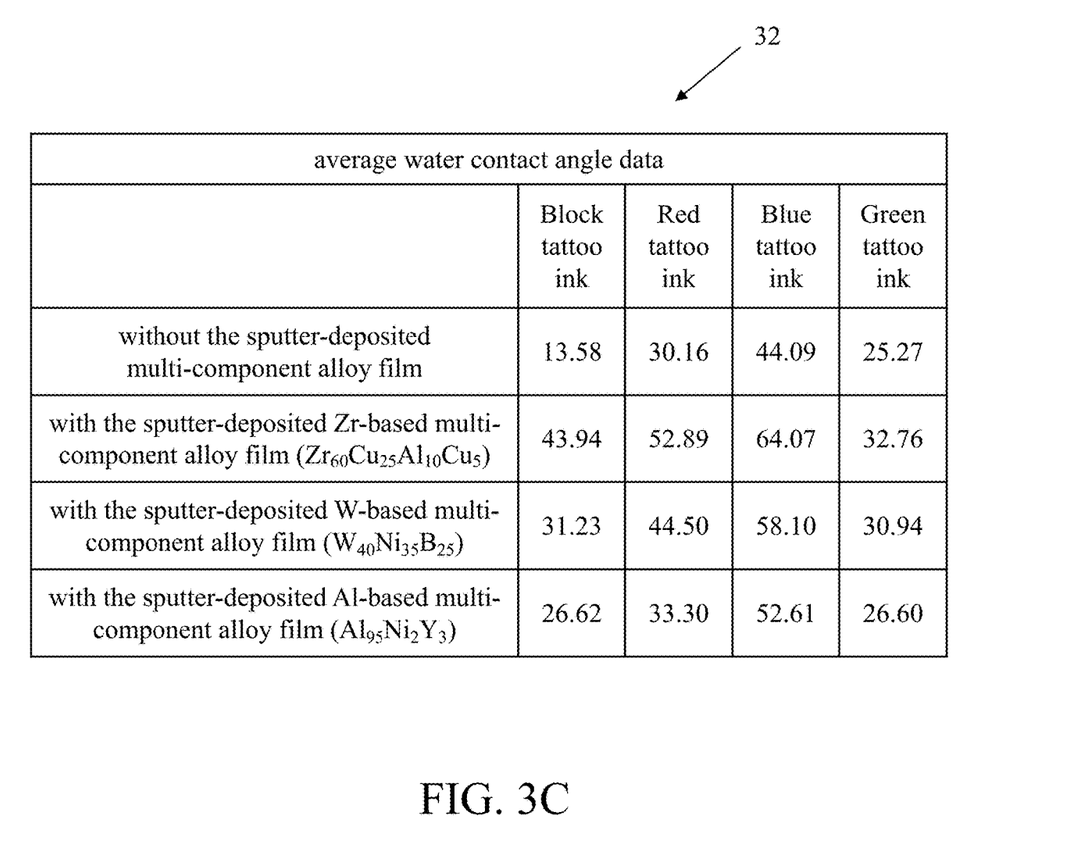
FIG. 3C shows the average water contact angle of different tattoo inks of different tattoo needle structures of the present invention.

Please refer to FIG. 3A to FIG. 3C, wherein FIG. 3A and FIG. 3B show water contact angles of different tattoo inks of different tattoo needle structures of the present invention, and FIG. 3C shows the average water contact angle of different tattoo inks of different tattoo needle structures of the present invention.

In FIG. 3A, the experimental data table 31 includes the water contact angles formed between the needle tips without the sputter-deposited multi-component alloy film and the tattoo ink after the tattoo needle is dipped into the tattoo ink five times, and the water contact angles formed between the needle tips with the sputter-deposited Zr-based multi-component alloy film including an element combination of Zr, Cu, Al, and Ni, and the tattoo ink after the tattoo needle is dipped into the tattoo ink five times, wherein the tattoo ink is the black tattoo ink, the red tattoo ink, the blue tattoo ink, or the green tattoo ink. For actual experimental data, please refer to the data presented in FIG. 3A, which is not repeated here.

In FIG. 3B, the experimental data table 31 includes the water contact angles formed between the needle tips with the sputter-deposited W-based multi-component alloy film including an element combination of W, Ni, and B, and the tattoo ink after the tattoo needle is dipped into the tattoo ink five times, and the water contact angles formed between the needle tips with the sputter-deposited Al-based multi-component alloy film including an element combination of Al, Ni, and Y, and the tattoo ink after the tattoo needle is dipped into the tattoo ink five times, wherein the tattoo ink is the black tattoo ink, the red tattoo ink, the blue tattoo ink, or the green tattoo ink. For actual experimental data, please refer to the data presented in FIG. 3B, which is not repeated here.

In FIG. 3C, the average data table 32 includes the average water contact angle formed between the needle tips without the sputter-deposited multi-component alloy film and the tattoo ink after the tattoo needle is dipped into the tattoo ink, the average water contact angle formed between the needle tips with the sputter-deposited Zr-based multi-component alloy film including an element combination of Zr, Cu, Al, and Ni, and the tattoo ink after the tattoo needle is dipped into the tattoo ink, the average water contact angle formed between the needle tips with the sputter-deposited W-based multi-component alloy film including an element combination of W, Ni, and B, and the tattoo ink after the tattoo needle is dipped into the tattoo ink, and the average water contact angle formed between the needle tips with the sputter-deposited Al-based multi-component alloy film including an element combination of Al, Ni, and Y, and the tattoo ink after the tattoo needle is dipped into the tattoo ink, wherein the tattoo ink is the black tattoo ink, the red tattoo ink, the blue tattoo ink, or the green tattoo ink.

According to the average data table 32, it can be obtained that the average water contact angle formed between the needle tips without the sputter-deposited multi-component alloy film and the black tattoo ink after the tattoo needle is dipped into the black tattoo ink, the average water contact angle formed between the needle tips without the sputter-deposited multi-component alloy film and the red tattoo ink after the tattoo needle is dipped into the red tattoo ink, the average water contact angle formed between the needle tips without the sputter-deposited multi-component alloy film and the blue tattoo ink after the tattoo needle is dipped into the blue tattoo ink, and the average water contact angle formed between the needle tips without the sputter-deposited multi-component alloy film and the green tattoo ink after the tattoo needle is dipped into the green tattoo ink, are the lowest values. It indicates that the needle tips of the tattoo needle without the sputter-deposited multi-component alloy film has poor hydrophobicity. That is, the tattoo ink sticks to the needle tips of the tattoo needle easily.

According to the average data table 32, it can be obtained that the average water contact angle formed between the needle tips with the sputter-deposited Zr-based multi-component alloy film and the black tattoo ink after the tattoo needle is dipped into the black tattoo ink, the average water contact angle formed between the needle tips with the sputter-deposited Zr-based multi-component alloy film and the red tattoo ink after the tattoo needle is dipped into the red tattoo ink, the average water contact angle formed between the needle tips with the sputter-deposited Zr-based multi-component alloy film and the blue tattoo ink after the tattoo needle is dipped into the blue tattoo ink, and the average water contact angle formed between the needle tips with the sputter-deposited Zr-based multi-component alloy film and the green tattoo ink after the tattoo needle is dipped into the green tattoo ink, are the highest values. It indicates that the needle tips of the tattoo needle with the sputter-deposited Zr-based multi-component alloy film has higher hydrophobicity. That is, the tattoo ink does not stick to the needle tips of the tattoo needle easily.

Figure 4:
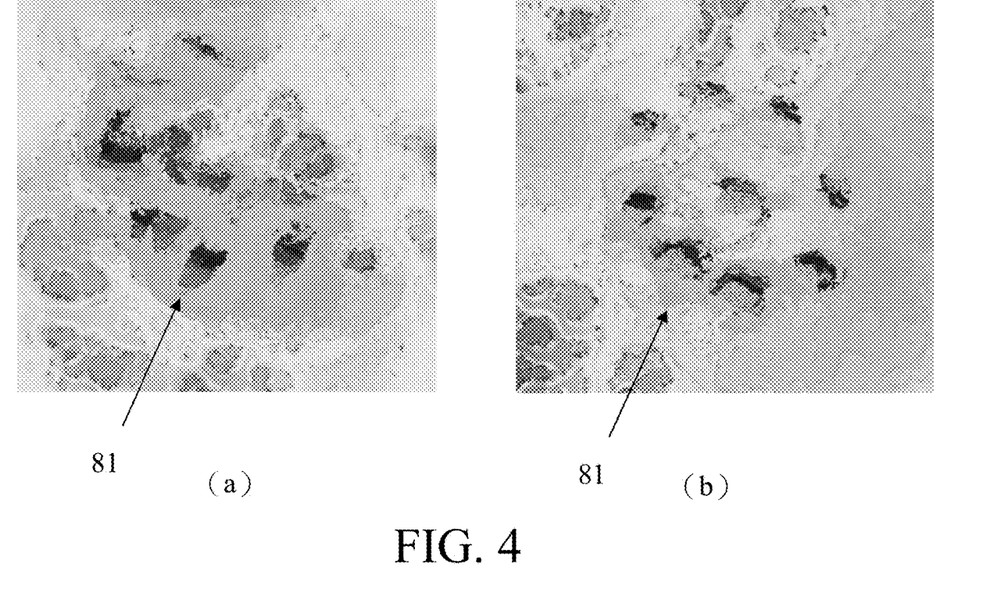
FIG. 4 shows a comparison diagram of the actual wound created by the needle tips without and with the sputter-deposited multi-component alloy film according to the tattoo needle structure of the present invention.
Figure 5:
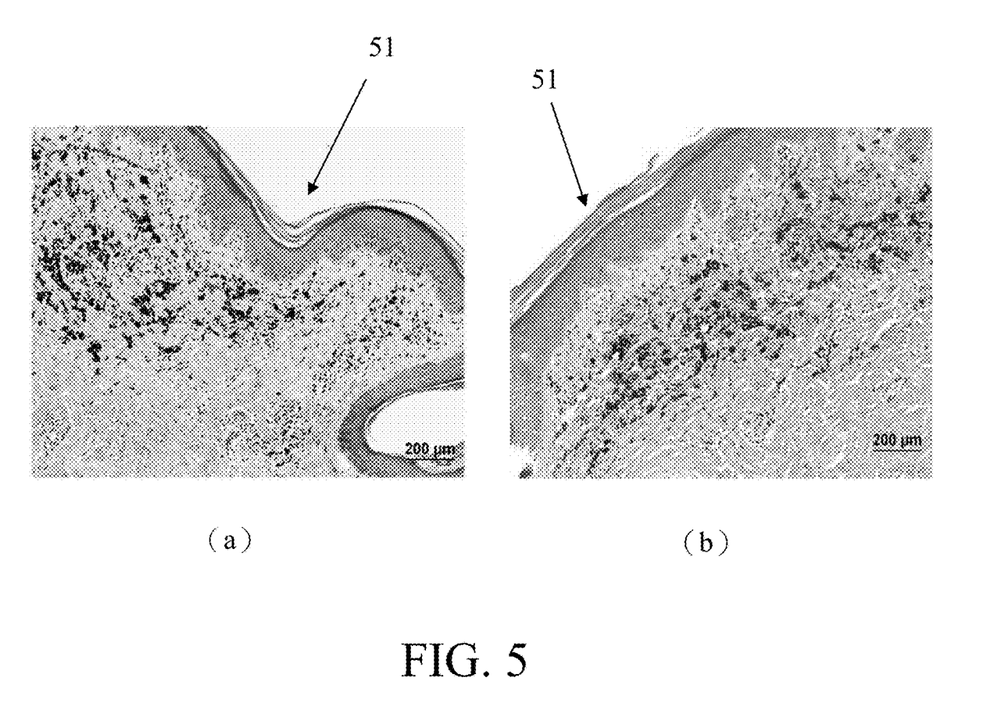
FIG. 5 shows a comparison diagram of the skin tissue tattooed by the needle tips without and with the sputter-deposited multi-component alloy film according to the tattoo needle structure of the present invention.

Please refer to FIG. 4 and FIG. 5, wherein FIG. 4 shows a comparison diagram of the actual wound created by the needle tips without and with the sputter-deposited multi-component alloy film according to the tattoo needle structure of the present invention, and FIG. 5 shows a comparison diagram of the skin tissue tattooed by the needle tips without and with the sputter-deposited multi-component alloy film according to the tattoo needle structure of the present invention.

Part (a) of FIG. 4 shows the wound 81 created by the needle tips of the tattoo needle without the sputter-deposited multi-component alloy film. Part (b) of FIG. 4 shows the wound 81 created by the needle tips of the tattoo needle with the sputter-deposited Zr-based multi-component alloy film. It can be clearly seen that the size of the wound 81 created by the needle tips of the tattoo needle with the sputter-deposited Zr-based multi-component alloy film (shown in part (b) of FIG. 4) is smaller than that created by the needle tips of the tattoo needle without the sputter-deposited multi-component alloy film (shown in part (b) of FIG. 4).

Part (a) of FIG. 5 shows that there is still an allergic inflammation reaction occurring on the skin 51 after six days of tattooing performed by the needle tips of the tattoo needle without the sputter-deposited multi-component alloy film. Part (b) of FIG. 5 shows that there is no allergic inflammation reaction occurring on the skin 51 after six days of tattooing performed by the needle tips of the tattoo needle with the sputter-deposited Zr-based multi-component alloy film (shown in part (a) of FIG. 5), while (shown in part (b) of FIG. 5).

Therefore, in the present invention, the tattoo needle having the needle tips with the sputter-deposited Zr-based multi-component alloy film including an element combination of Zr, Cu, Al, and Ni, is used for the subsequent description of the present invention. The multi-component alloy film can provide the tattoo needle with characteristics of durability, non-shelling, non-toxicity and low exertion force, so that the tattoo needle with the sputter-deposited multi-component alloy film can reduce the size of the wound on the skin after the skin is punctured, the duration of allergy and inflammation of the skin after tattooing, and the risks caused by the tattooing process.

Figure 6A:
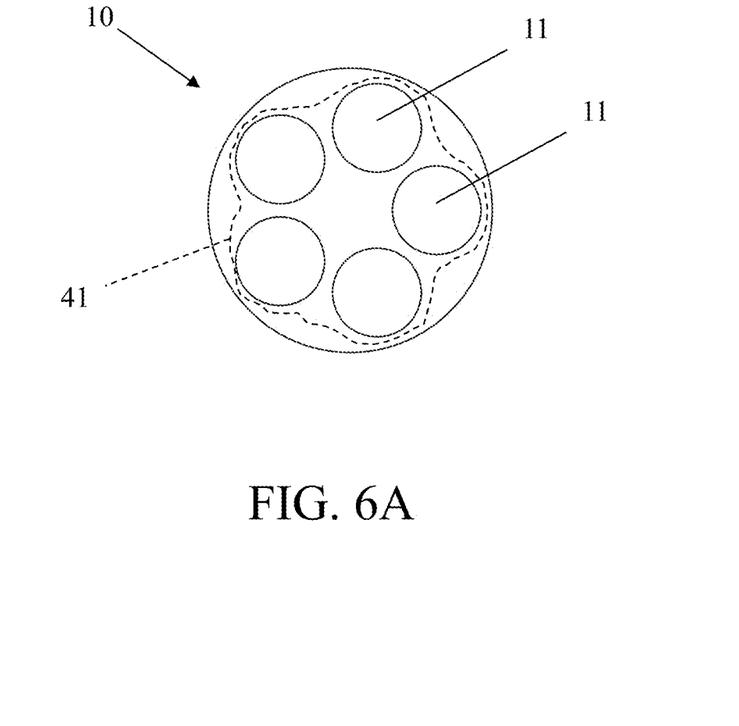
FIG. 6A is a schematic diagram of ink adsorption after the tattoo needle of the tattoo needle structure of the present invention is dipped into the tattoo ink, wherein the needle tips are without the sputter-deposited multi-component alloy film.
Figure 6B:
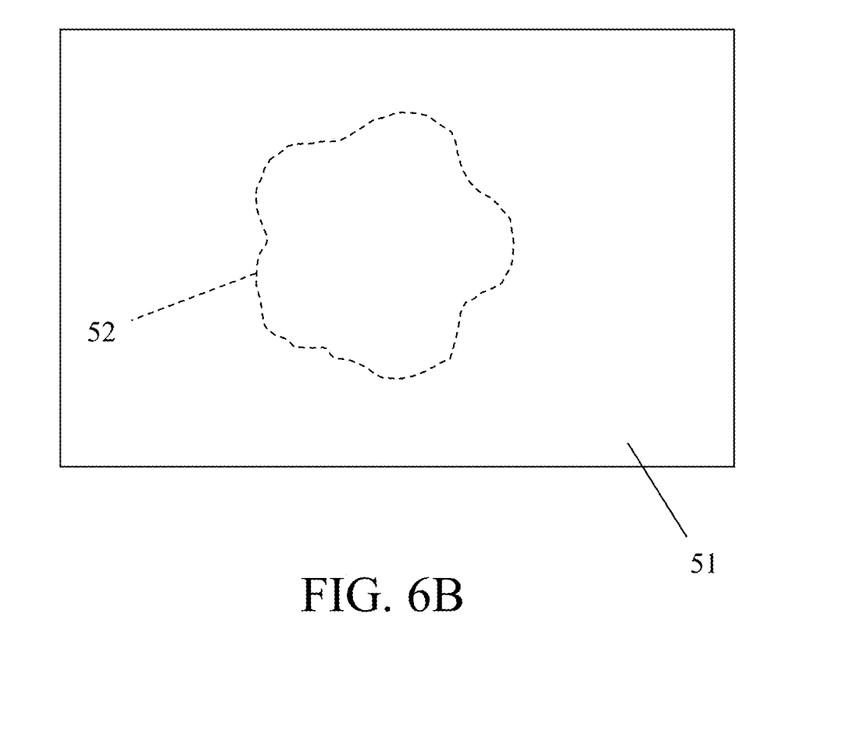
FIG. 6B is a schematic diagram showing a tattooed area of the tattoo needle of the tattoo needle structure of the present invention, wherein the needle tips are without the sputter-deposited multi-component alloy film.

Please refer to FIG. 6A and FIG. 6B. FIG. 6A is a schematic diagram of ink adsorption after the tattoo needle of the tattoo needle structure of the present invention is dipped into the tattoo ink, wherein the needle tips are without the sputter-deposited multi-component alloy film. FIG. 6B is a schematic diagram showing a tattooed area of the tattoo needle of the tattoo needle structure of the present invention, wherein the needle tips are without the sputter-deposited multi-component alloy film.

From the above, the needle tips 11 have poor hydrophobicity since the needle tips 11 of the tattoo needle 10 are without the sputter-deposited multi-component alloy film. That is, the tattoo ink sticks to the needle tips 11 of the tattoo needle 10 easily after the tattoo needle 10 is dipped into the tattoo ink. In FIG. 6A, the adsorption zone 41 of the tattoo ink includes the ink holding space 12 formed by the needle tips 11 of the tattoo needle 10, the gaps between the needle tips 11 of the tattoo needle 10, and the surfaces of the needle tips 11 of the tattoo needle 10 due to the low hydrophobicity of the needle tips 11 of the tattoo needle 10 and the cohesion of the tattoo ink. FIG. 6A is a schematic representation in a more exaggerated manner.

After the tattoo needle 10 is dipped into the tattoo ink, the needle tips 11 of the tattoo needle 10 puncture the skin 51. The adsorption zone 41 of the tattoo ink includes the ink holding space 12 formed by the needle tips 11 of the tattoo needle 10, the gap between the needle tips 11 of the tattoo needle 10 and the surface of the needle tips 11 of the tattoo needle 10, so the dyeing area 52 of the skin 51 with the tattoo ink is much larger than the cross-sectional area of the ink holding space 12 in FIG. 6B, and the tattoo ink cannot be concentrated in the ink holding space 12. Thus, the tattoo result on the skin after tattooing is blurred. In other words, the resolution of the tattoo is low.

Figure 7A:
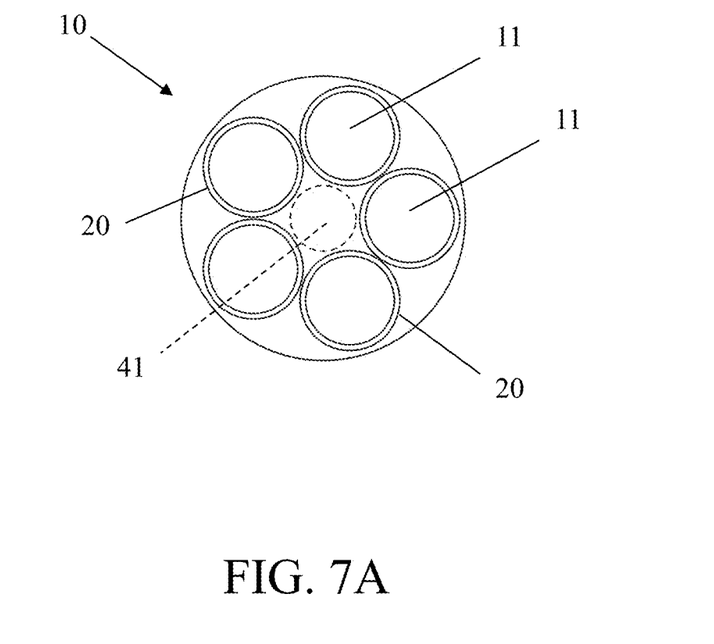
FIG. 7A is a schematic diagram of ink adsorption after the tattoo needle of the tattoo needle structure of the present invention is dipped into the tattoo ink, wherein the needle tips are with the sputter-deposited multi-component alloy film.
Figure 7B:
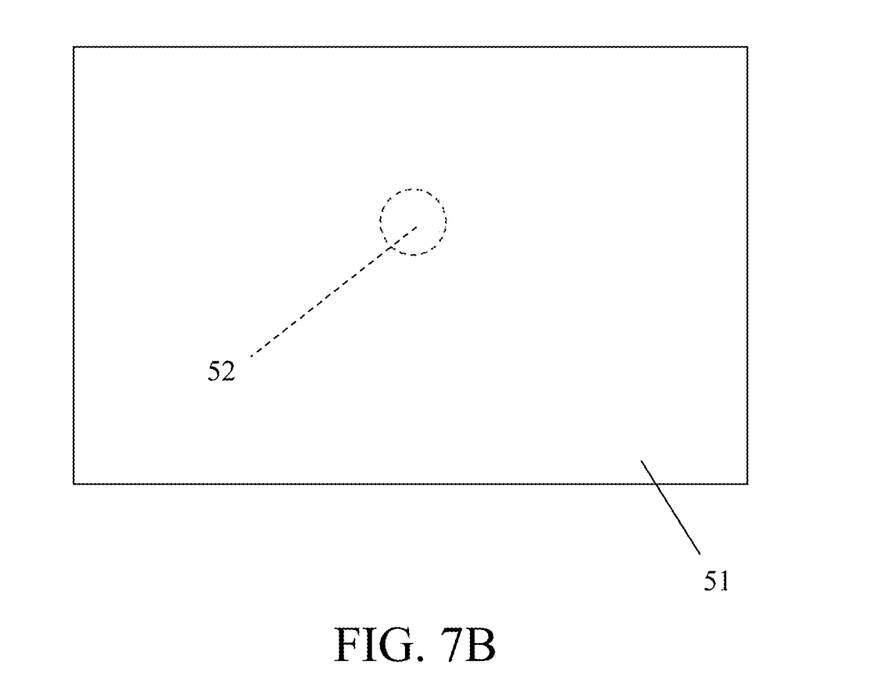
FIG. 7B is a schematic diagram showing a tattooed area of the tattoo needle of the tattoo needle structure of the present invention, wherein the needle tips are with the sputter-deposited multi-component alloy film.

Please refer to FIG. 7A and FIG. 7B. FIG. 7A is a schematic diagram of ink adsorption after the tattoo needle of the tattoo needle structure of the present invention is dipped into the tattoo ink, wherein the needle tips are with the sputter-deposited multi-component alloy film. FIG. 7B is a schematic diagram showing a tattooed area of the tattoo needle of the tattoo needle structure of the present invention, wherein the needle tips are with the sputter-deposited multi-component alloy film.

From the above, the needle tips 11 of the tattoo needle 10 have the higher hydrophobicity since the sputter-deposited multi-component alloy film on the needle tips 11 of the tattoo needle 10 (the multi-component alloy film is a Zr-based multi-component alloy film including an element combination of Zr, Cu, Al, and Ni). That is, the tattoo ink does not stick to the needle tips 11 of the tattoo needle 10 easily after the tattoo needle 10 is dipped into the tattoo ink. In FIG. 7A, the adsorption zone 41 of the tattoo ink only includes the ink holding space 12 formed by the needle tips 11 of the tattoo needles 10 because the needle tips 11 of the tattoo needles 10 have the higher hydrophobicity, and the cohesive property of the tattoo ink. FIG. 7A is a schematic representation in a more exaggerated manner. In fact, there is more or less tattoo ink sticking to the needle tips 11 of the tattoo needle 10, but the tattoo ink does not stick to the surfaces of the needle tips 11 of the tattoo needle 10, which are not on the ink holding space 12, and the gaps between the needle tips 11 of the tattoo needle 10 through the hydrophobicity of the multi-component alloy film.

After the tattoo needle 10 is dipped into the tattoo ink, the needle tips 11 of the tattoo needle 10 puncture the skin 51. The adsorption zone 41 of the tattoo ink only includes the ink holding space 12 formed by the needle tips 11 of the tattoo needle 10, so the dyeing area 52 of the skin 51 with the tattoo ink is slightly larger than the cross-sectional area of the ink holding space 12 in FIG. 5B, and the tattoo ink can be concentrated in the ink holding space 12. Thus, the tattoo result on the skin after tattooing is clearer. In other words, the resolution of the tattoo is higher.

Figure 8:
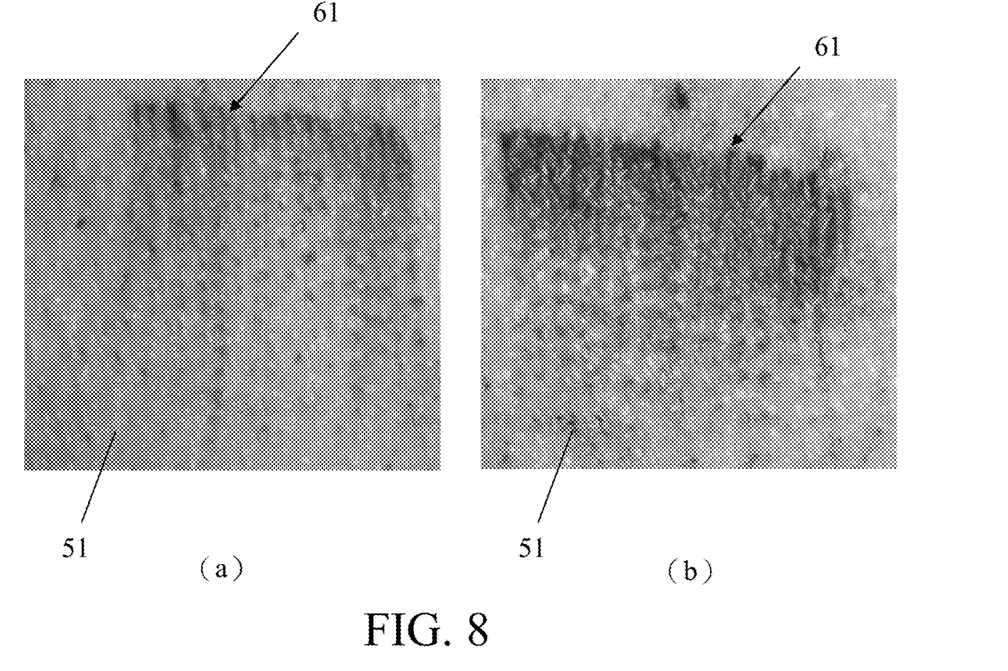
FIG. 8 and FIG. 9 show a comparison diagram of actual tattooing results performed by the needle tips without and with the sputter-deposited multi-component alloy film according to the tattoo needle structure of the present invention.
Figure 9:
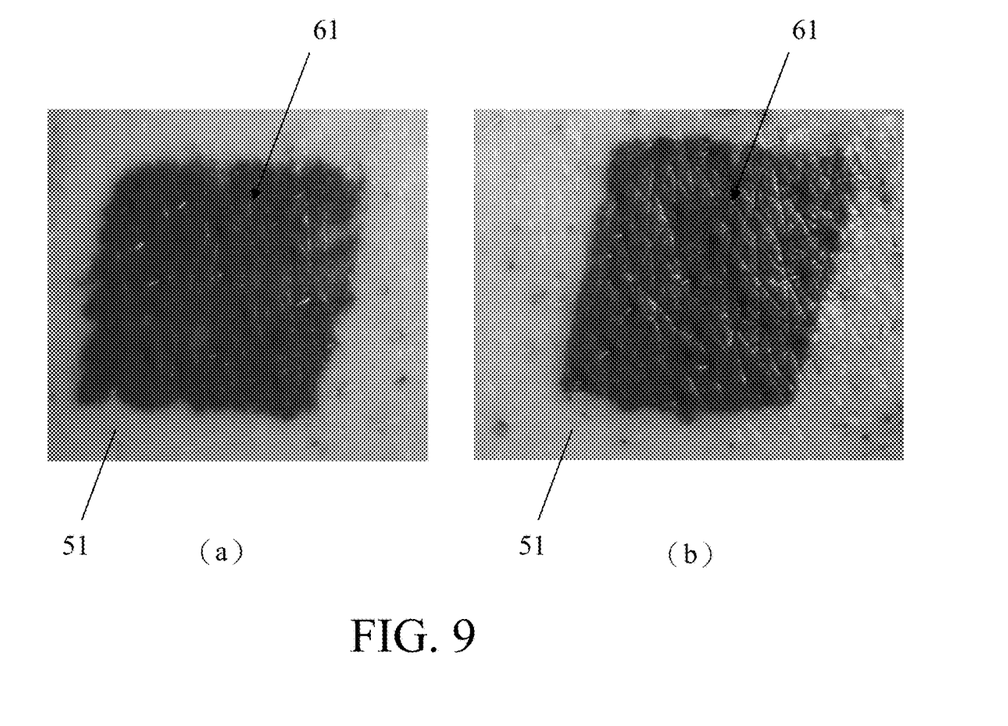

Please refer to FIG. 8 and FIG. 9. FIG. 8 and FIG. 9 show a comparison diagram of actual tattooing results performed by the needle tips without and with the sputter-deposited multi-component alloy film according to the tattoo needle structure of the present invention.

Part (a) of FIG. 8 shows a gradient pattern 61 of the tattoo formed by performing many skin punctures with the actual use of the tattoo needle 10 after it is dipped into tattoo ink, wherein the needle tips 11 of the tattoo needle 10 are without the sputter-deposited multi-component alloy film. Part (b) of FIG. 8 shows a gradient pattern 61 of the tattoo formed by performing many skin punctures with the actual use of the tattoo needle 10 after it is dipped into tattoo ink, wherein the needle tips 11 of the tattoo needle 10 are with the sputter-deposited multi-component alloy film (the multi-component alloy film is a Zr-based multi-component alloy film including an element combination of Zr, Cu, Al, and Ni). It can be clearly seen that the tattoo result presented by each skin puncture in part (a) of FIG. 8 is blurrier than that in the part (b) of FIG. 8, and it can also be seen that the color saturation of each skin puncture in part (a) of FIG. 8 is poor than that in the part (b) of FIG. 8. From the above, it can be seen that the tattoo result of part (a) of FIG. 8 is caused due to the fact that the dyeing area of the skin with the tattoo ink is much larger than the cross-sectional area of the ink holding space, and the tattoo result of part (b) of FIG. 8 is caused due to the fact that the dyeing area of the skin with the tattoo ink is concentrated in the cross-sectional area of the ink holding space.

Part (a) of FIG. 9 shows the result of a tattooed area formed with the actual use of the tattoo needle 10, wherein the needle tips 11 of the tattoo needle 10 are without the sputter-deposited multi-component alloy film. Part (b) of FIG. 9 shows the result of a tattooed area formed with the actual use of the tattoo needle 10, wherein the needle tips 11 of the tattoo needle 10 are with the sputter-deposited multi-component alloy film (the multi-component alloy film is a Zr-based multi-component alloy film including an element combination of Zr, Cu, Al, and Ni). It can be clearly seen that the tattooed area 62 after tattooing shown in part (a) of FIG. 9 cannot clearly show the original appearance of the skin, relative to part (b) of FIG. 9. That is, the result of the tattoo area 62 after tattooing in part (a) of FIG. 9 is blurrier than that in the part (b) of FIG. 9. In other words, the resolution of the tattooed area in the part (a) of FIG. 9 is lower than that in part (b) of FIG. 9. From the above, it can be also seen that the result of part (a) of FIG. 9 is caused due to the fact that the dyeing area of the skin with the tattoo ink is much larger than the cross-sectional area of the ink holding space, and the result of part (b) of FIG. 9 is caused due to the fact that the dyeing area of the skin with the tattoo ink is concentrated in the cross-sectional area of the ink holding space.

Based on FIG. 8 and FIG. 9, it can be clearly seen that the color saturation of the tattoo created by the needle tips 11 of the tattoo needle 10 with the sputter-deposited multi-component alloy film is higher than that created by the needle tips 11 of the tattoo needle 10 without the sputter-deposited multi-component alloy film, so the needle tips 11 of the tattoo needle 10 without the sputter-deposited multi-component alloy film need to perform more skin punctures to achieve the color saturation similar to the color saturation created by the needle tips 11 of the tattoo needle 10 with the sputter-deposited multi-component alloy film. Since the needle tips 11 of the tattoo needle 10 without the sputter-deposited multi-component alloy film need to perform more skin punctures to achieve the color saturation similar to the color saturation created by the needle tips 11 of the tattoo needle 10 with the sputter-deposited multi-component alloy film, the needle tips 11 of the tattoo needle 10 without the sputter-deposited multi-component alloy film need to use more tattoo ink.

Figure 10:
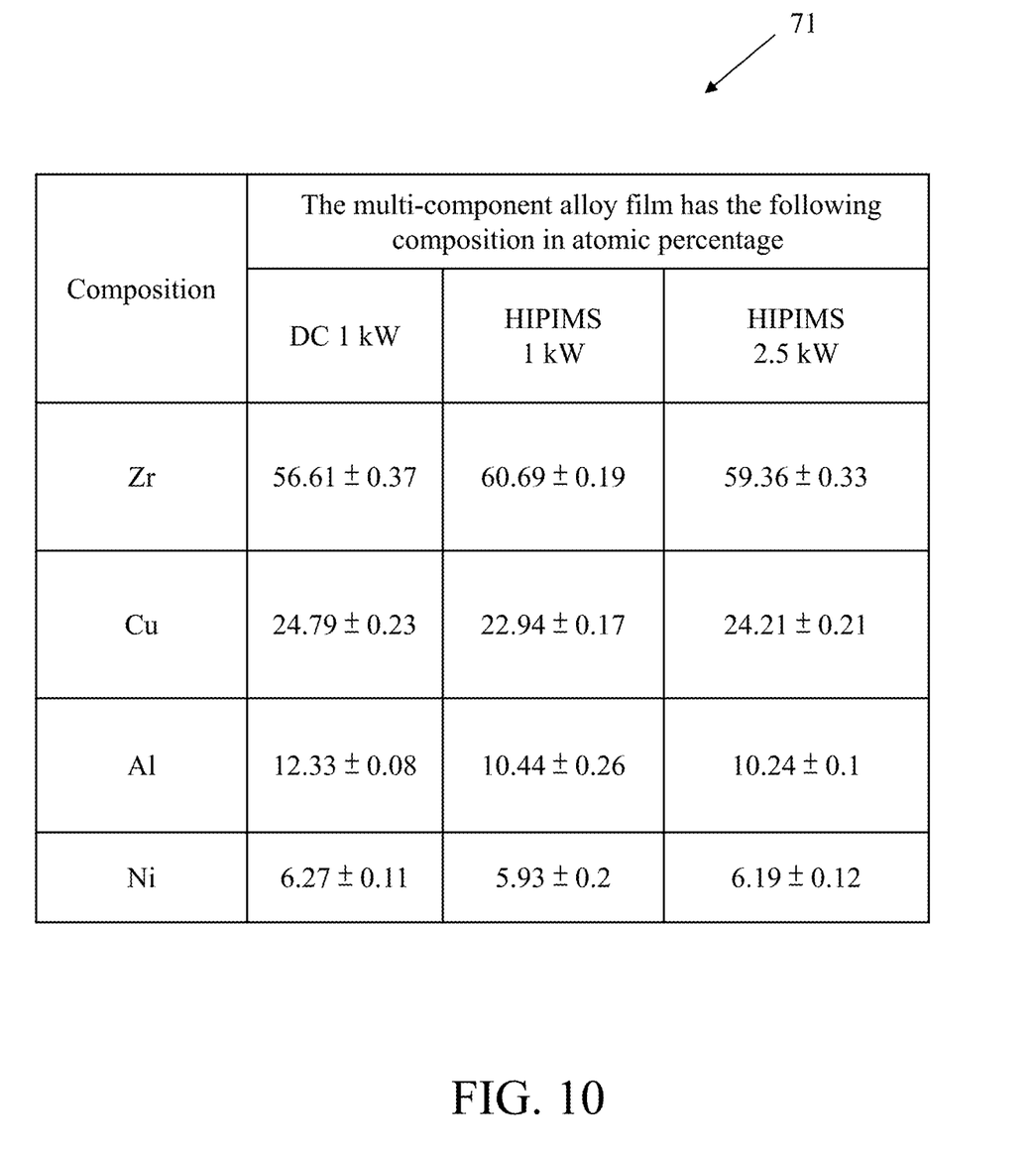
FIG. 10 shows the atomic percentages of the multi-component alloy film of the tattoo needle structure of the present invention.

Please refer to FIG. 10. FIG. 10 shows the atomic percentages of the multi-component alloy film of the tattoo needle structure of the present invention.

In FIG. 10, the element combination table 71 includes the atomic percentages of the multi-component alloy film made by different sputtering technology and different process parameters. The aforementioned multi-component alloy film is deposited on the needle tips 11 of the tattoo needle 10 by the sputtering technology, and the sputtering technology includes DC magnetron sputtering technology and high-power impulse magnetron sputtering (HIPIMS) technology. Under the condition that the sputtering technology is DC magnetron sputtering technology with the working power of 1 kW, the multi-component alloy film has the following composition in atomic percentage: Zr is 56.61±0.37 at %, Cu is 24.79±0.23 at %, Al is 12.33±0.08 at %, and Ni is 6.27±0.11 at %. This is for illustration only, and does not limit the application scope of the present invention.

Under the condition that the sputtering technology is the high-power impulse magnetron sputtering technology with the working power of 1 kW, the multi-component alloy film has the following composition in atomic percentage: Zr is 60.69±0.19 at %, Cu is 22.94±0.17 at %, Al is 10.44±0.26 at %, and Ni is 5.93±0.2 at %. This is for illustration only, and does not limit the application scope of the present invention.

Under the condition that the sputtering technology is the high-power impulse magnetron sputtering technology, and the process parameters used by the high-power impulse magnetron sputtering technology include a vacuum degree of $6.7 \times 10^{-5}$ Pa, a working pressure of 3.7 mTorr, a working power of 2.5 kW, a rotation rate of 1 rpm, and the duration and bias value respectively set in the following order: a bias value of 600V for a 100-second duration, a bias value of 500V for a 100-second duration, a bias value of 400V for a 100-second duration, a bias value of 300V for a 100-second duration, a bias value of 200V for a 100-second duration, a bias value of 100V for a 100-second duration, and a bias value of 60V for a 18-second duration, the multi-component alloy film has the following composition in atomic percentage: Zr is 59.36±0.33 at %, Cu is 24.21±0.21 at %, Al is 10.24±0.1 at %, and Ni is 6.19±0.12 at %.

In summary, it can be seen that the difference between the present invention and the prior art is that the tattoo needle has the plurality of needle tips, the arrangement of the needle tips forms the ink holding space, and the multi-component alloy film is disposed on the needle tips by sputtering technology; when the tattoo needle is dipped into the tattoo ink, the tattoo ink does not stick to the surface of the multi-component alloy film due to the hydrophobic property of the multi-component alloy film, and the tattoo ink is concentrated and contained in the ink holding space due to the cohesive property of the tattoo ink, so that the dyeing area of the skin with the tattoo ink is the cross-sectional area of the ink holding space when the tattoo needle is dipped into tattoo ink and the tattooing process is performed.

By the above-mentioned technical solution, the present invention can solve the problem of insufficient accuracy for the existing tattoo needle tools used for outlining a tattoo and achieve the technical effect of improving the contouring resolution of a tattoo.

The present invention disclosed herein has been described by means of specific embodiments. However, numerous modifications, variations and enhancements can be made thereto by those skilled in the art without departing from the spirit and scope of the disclosure set forth in the claims.

What is claimed is:

1. A tattoo needle structure, comprising:
    a tattoo needle, having a plurality of needle tips, an ink holding space being formed through an arrangement of the plurality of needle tips; and
    a multi-component alloy film, deposited on the plurality of needle tips by sputtering technology, wherein a deposited thickness of the multi-component alloy film is between 50 nm and 200 nm;
    wherein when the tattoo needle is dipped into tattoo ink, the tattoo ink does not stick to a surface of the multi-component alloy film by a hydrophobic property of the multi-component alloy film, and the tattoo ink is concentrated and contained in the ink holding space by the arrangement of the plurality of needle tips and cohesion of the tattoo ink, so that when the tattoo needle is dipped into the tattoo ink and a tattooing process is performed, a dyeing area of skin with the tattoo ink is a cross-sectional area of the ink holding space.

2. The tattoo needle structure according to claim 1, wherein an element combination of the multi-component alloy film includes Zr, Cu, Al, and Ni.

3. The tattoo needle structure according to claim 1, wherein the multi-component alloy film has the following composition in atomic percentage: Zr is 56.61±0.37 at %, Cu is 24.79±0.23 at %, Al is 12.33±0.08 at %, and Ni is 6.27±0.11 at % under the condition that the sputtering technology is DC magnetron sputtering technology with a working power of 1 kW.

4. The tattoo needle structure according to claim 1, wherein the multi-component alloy film has the following composition in atomic percentage: Zr is 60.69±0.19 at %, Cu is 22.94±0.17 at %, Al is 10.44±0.26 at %, and Ni is 5.93±0.2 at % under the condition that the sputtering technology is high-power impulse magnetron sputtering technology with a working power of 1 kW.

5. The tattoo needle structure according to claim 1, wherein the multi-component alloy film has the following composition in atomic percentage: Zr is 59.36±0.33 at %, Cu is 24.21±0.21 at %, Al is 10.24±0.1 at %, and Ni is 6.19±0.12 at % under the condition that the sputtering technology is high-power impulse magnetron sputtering technology with a working power of 2.5 kW.

6. The tattoo needle structure according to claim 1, wherein the sputtering technology is high-power impulse magnetron sputtering technology, and process parameters used by the high-power impulse magnetron sputtering technology include a vacuum degree of $6.7 \times 10^{-5}$ Pa, a working pressure of 3.7 mTorr, a working power of 2.5 kW, a rotation rate of 1 rpm, and the duration and bias value respectively set in the following order: a bias value of 600V for a 100-second duration, a bias value of 500V for a 100-second duration, a bias value of 400V for a 100-second duration, a bias value of 300V for a 100-second duration, a bias value of 200V for a 100-second duration, a bias value of 100V for a 100-second duration, and a bias value of 60V for a 18-second duration.

7. The tattoo needle structure according to claim 1, wherein the plurality of needle tips of the tattoo needle is in a circular arrangement, and the inside of the circular arrangement of the plurality of needle tips is the ink holding space.

8. The tattoo needle structure according to claim 7, wherein an additional needle tip is further provided in the ink holding space.

* * * * *